United States Patent [19]

Baker et al.

[11] Patent Number: 4,574,083

[45] Date of Patent: Mar. 4, 1986

[54] **ISOLATES OF PYTHIUM SPECIES WHICH ARE ANTAGONISTIC TO *PYTHIUM ULTIMUM***

[75] Inventors: Ralph Baker, Fort Collins, Colo.; Ran Lifshitz, Ramat Chen, Israel

[73] Assignee: Colorado State University Research Foundation, Fort Collins, Colo.

[21] Appl. No.: 555,941

[22] Filed: Nov. 29, 1983

[51] Int. Cl.⁴ .................. A01N 63/00; C12N 1/14; C12N 15/00; C12R 1/648

[52] U.S. Cl. ............................... 424/93; 47/58; 435/254; 435/172.1; 435/911

[58] Field of Search ............... 435/254, 911, 29, 34; 47/58; 424/93, 172.1

[56] References Cited

PUBLICATIONS

Vaartaja, O., "Inhibition of *Pythium ultimum* in Molecular Fractions from Gel Filtration of Soil Extracts", Chem. Abstracts 82:3204y, 1975.

Vesely, D., "An Agent Applied to Sugar Beet Seed for the Stimulation of Germination-Protection Against Leaf Scorch", Chem. Abstracts 99:189795w, 1983.

Lifshitz et al., "Soil Suppressiveness to a Plant Pathogenic Pythium Species", Phytopathology 74(9), 1054–1061, 1984.

*Primary Examiner*—Thomas G. Wiseman
*Assistant Examiner*—R. L. Teskin
*Attorney, Agent, or Firm*—Roman Saliwanchik

[57] ABSTRACT

Novel isolates of Pythium are provided which are antagonistic to indigenous plant pathogenic species of *Pythium ultimum* from soil. The isolates suppress the growth of *P. ultimum* when added to soil and are particularly useful to protect seedlings from damping-off disease caused by *P. ultimum*.

5 Claims, 3 Drawing Figures

ISOLATES OF PYTHIUM SPECIES WHICH ARE ANTAGONISTIC TO *PYTHIUM ULTIMUM*

The present invention is directed to novel isolates of Pythium which suppress the growth and activity of *Pythium ultimum*, and other Pythium and Phytophthora.

Certain species of Pythium are pathogenic to a variety of plant hosts. For example, the problems of pre- and post-emergence damping-off and root rot of many important crops have been attributed to Pythium. Pythium may be controlled by chemical fungicides; however, as with most agricultural chemicals, environmental pollution may cause not only human and animal health hazards, but also have phytotoxic effects on useful and/or desirable vegetation.

It is therefore desirable to develop alternative methods of controlling pathogenic species of Pythium and other fungi utilizing controllable biological agents which are economically feasible to produce and use.

It is thus an object of the present invention to provide a novel method for biologically controlling pathogenic Pythium and Phytophthora species.

It is another object of the present invention to provide novel isolates of Pythium species which are antagonistic to *Pythium ultimum*.

It is a further object of the present invention to provide novel isolates of Pythium species which induce suppressiveness to *Pythium ultimum* growth in soil.

Figure 1:
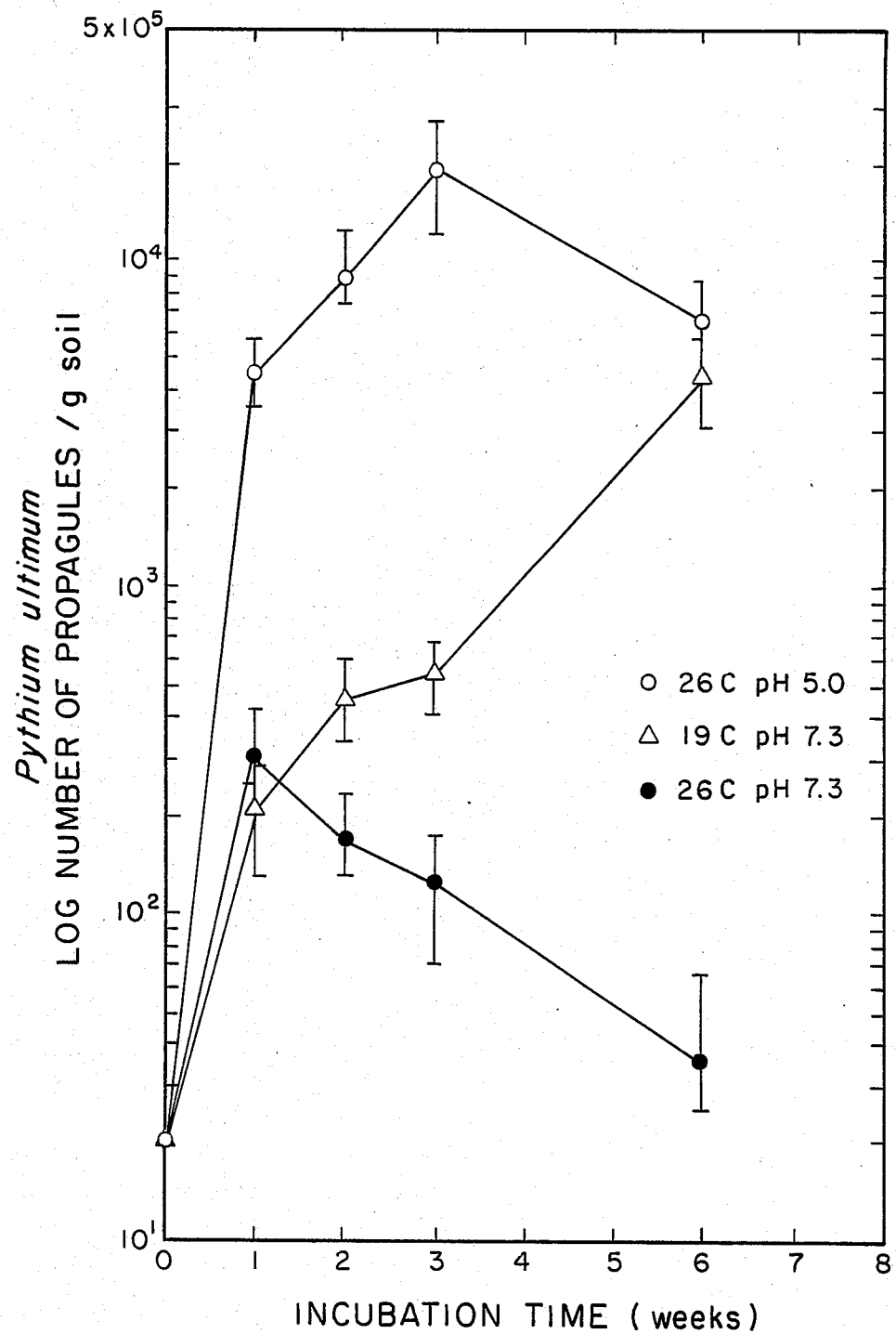
FIG. 1 is a plot of the time dependence of the *Pythium ultimum* propagule density in soil at various temperatures and pHs enriched with bean leaf meal.

The present invention provides a method for isolating novel mycoparasitic fungal strains of Pythium sp. comprising the steps of screening a culture of indigenous *Pythium ultimum* and isolating colonies capable of suppressing growth and activity of *P. ultimum* and other Pythium and Phytophthora species which are pathogenic to desirable vegetation. The present invention further provides biologically pure cultures of *P. ultimum* having the identifying characteristics of isolates N2 and N3 (ATCC Deposit Nos. 20692 and 20693, respectively) and which are capable of suppressing the growth and activity in soil of *P. ultimum* and other Pythium and Phytophthora species which are pathogenic to desirable vegetation.

The present invention concerns the isolation of novel Pythium species from soils containing an indigenous population of Pythium sp. The isolate designated N3 has the properties listed below in TABLE 1. Isolate N2 has properties similar to N3 except that it rarely produces oogonia and oospores.

TABLE 1

| PROPERTIES OF ISOLATES N3 | |
|---|---|
| Radial Growth | Less than 25 mm in diameter after 4 days incubation at 26° C. |
| Growth on Potato Dextrose Agar | Rosette habit |
| Sporangia | Germinated by germ tube, acrogenous and spherical or intercalary and lemon-shaped (12-22.5 micrometers, average 16.2 micrometers). |
| Temperature Range of Optimal Radial Growth | 7 to 40° C. with optimal at 30° C. |
| Sporulation on Oatmeal Agar | None |
| Sporulation on V-8 Broth | None |
| Sporulation on Water Culture with Sterile Bean Leaf Fragments (14 days at 26° in dark). | Positive |
| Zoospore Production | None |
| Oogonia | Acrogenous, smooth and spherical (18.5-23 micrometers, average 20.8 micrometers) 1-5 antheridia per oogonium. |
| Oospores | Aplerotic (18-20.5 micrometers, averaging 19.2 micrometers). Thick cell wall (>2 hm). |

The isolates N2 and N3 do not match the morphology or physiological behavior of any reported species of Pythium. Isolates N2 and N3 have been deposited with the American Type Culture Collection, Rockville, MD., under Deposit Nos. 20692 and 20693, respectively.

The novel Pythium isolates according to the present invention may be isolated from soil containing an indigenous population of Pythium sp. The isolates designated N2 and N3 above were isolated from Nunn sandy loam soil from Nunn region, Colorado in two batches. The first batch, designated B, had a pH of 6.8 collected in midsummer. The second soil batch, designated A, had a pH of 7.3 collected in early spring. Both batches were characterized as having less than 1% lime, conductivity of 0.4 mmhos/cm; organic matter, 1.1%; one milligram per gram nitrogen (as $NO_3$); 9 micrograms/gram extractible zinc; and 3.2 micrograms per gram extractible iron. The soil was air-dried, sieved through a 4 mm mesh screen and stored in covered containers.

The Pythium species in the soils were enriched by procedures described in Lifshitz and Hancock, *Plant Disease* 65, 828-829 (1981), disclosure of which is incorporated by reference herein. Nunn sandy loam soil (pH 7.3) was used either at its original pH or was acidified by mixing with 1N $H_2SO_4$ to give a soil pH of 5.0. Dry, mature green bean (*Phaseolus vulgaris* CV 'Pinto') leaves (ground and sieved through a 1 mm mesh screen), were incorporated into the soil (0.3 grams of leaves into 100 grams of soil). The soil was thoroughly mixed with 15% (weight/volume) sterile tap water (−0.3 bar) and the soils were placed in 6 by 9 cm glass jars (170 grams per jar, 3 jars per treatment) and covered with polyethylene sheets to reduce evaporation. The jars were incubated at the desired controlled temperature (19±1° C. or 26±1° C.) for seven days. At the end of the incubation period the soils were air-dried, ground and mixed. The soils were repeatedly amended and treated in this manner for a total of six incubation cycles. During this period soil samples from each jar were tested for Pythium propagule density by the soil drop method (Stanghellini, et al., *Phytopathology* 60, 551-552 (1970)) and by counting colony-forming units (cfu) on dilution plates on a selective medium as disclosed by Mircetich, et al., *Mycopathol. Mycol. Appl.* 50, 151-161 (1978). Isolates were designated N1 through N3. When tested for Trichoderma species, propagule density was determined on dilution plates on the selective medium disclosed by Elad, et al., *Phytoparasitica* 9, 59-67 (1981).

The isolates N1 through N3 were tested for pathogenicity against various plants. Each isolate was grown on potato dextrose agar for five days at 26° C. The agar disks (8 millimeters) with mycleium or sterile medium as controls, were placed in sterile soil at a depth of one centimeter. Five seeds of each of the various plants were placed directly on the agar disks in each of four pots per host. The pots were watered to −0.3 bar (15% w/v), covered with transparent mylar sheets and incubated at 19° C. (two pots per treatment) and 26° C. Counts of healthy seedlings were made after fourteen days. The Pythium isolate N1 was pathogenic and induced an 80-100% reduction in stand compared to noninoculated controls of the following plants: *Pisum sativum* cv 'Laxton Progress', *Pisum sativum* cv 'Early Frosty', *Phaseolus volgaris* cv 'Contender', *Cucumis sativus* L. cv. 'Straight Eight', *Citrullus lanatus* cv 'Dixii Queen', *Cucurbita sp.* cv 'Bush TABLE', *Raphanus sativus* cv 'Early Scarlet Globe', *Lactuca sativa* cv 'Early Curled' and *Medicago sativa* cv 'Titan'. Isolate N1 did not reduce significantly (pathogenicity probability (P)=0.05) the stand of *Triticum aestivum* cv 'Hermisillo' and *Hordeum volgare* cv 'Steptoe'. The two isolates designated N2 and N3 did not significantly reduce (P=0.05) the stands of any of the above plants and there was no evidence of infection by these isolates in any of the hosts tested.

The antagonistic activity of isolates N2 and N3 on indigenous *P. ultimum* were tested as follows.

Influence of Pythium isolates N2 and N3 on the Saprophytic Activity of *P. ultimum*

Isolates N2 and N3 were added to soil and incubated with control samples containing no isolates for two weeks with application of bean leaf meal at 0 and 7 days. The N2 and N3 isolates were grown on rolled oat and water medium (Hancock, *Hilgardia* 45, 107-122 (1977) at 26° for 14 days. Mycelial mats were removed and placed in sterile soil amended with bean leaf (0.3 grams per 100 grams of soil). Soil moisture was adjusted to 0.3 bar with sterile tap water. The soils were placed in a closed container incubated for 7 days at 26° C. At the end of the incubation period, the infested soils were air-dried, ground and sieved (one millimeter mesh screen). Counts of cfu of N2 and N3 isolates were determined by plate dilution method on the selective medium referenced above (Mircetich, et al.). The infested soil preparations were mixed in raw soil. Population densities of isolates N2 and N3 were estimated as about 100 cfu/gram soil by plate dilution on selective medium (the mixtures contained 1:25 and 1:30 infested soil preparations of isolates N2 and N3, respectively, in raw soil). The mixture was incubated two weeks at 26°.

In soils where N2 and N3 were not added, inoculum densities of *P. ultimum* increased from nondetectible levels (less than 25) to $5.2 \times 10^3$ (at 19° C.) or $5.4 \times 10^2$ (at 26° C.) (cfu/gram during the first week in soil A and $17-1.6 \times 10^4$ at 19° C.) or $5 \times 10^3$ (at 26° C.) cfu/gm in soil B. The results are summarized below in TABLE 2.

TABLE 2

Population densities of *Pythium ultimum* in soil incubated with two weekly applications of dried bean leaf meal over a two-week period.

| Soil Batch[a] | Temp. (C) | Pythium sp. Isolate Added | Incubation Time | | | |
|---|---|---|---|---|---|---|
| | | | 1 wk | | 2 wks | |
| | | | Small Cols.[b] (cfu/g × 100) | Large Cols.[c] (cfu/g × 100) | Small Cols.[b] (cfu/g × 100) | Large Cols.[c] (cfu/g × 100) |
| A | 19 | None | NDd z | 52 w | 4 y | 46 w |
| | | N2 | 100 v | 12 x | 380 st | ND z |
| | | N3 | 160 u | 10 x | 360 st | ND z |
| A | 26 | None | 0.4 z | 5 y | 43 w | 9 xy |
| | | N2 | 160 u | 0.2 y | 460 s | ND z |
| | | N3 | 190 u | 1 z | 430 s | 0.1 z |
| B | 19 | None | ND z | 160 u | ND z | 150 u |
| | | N2 | 110 v | 4 y | 510 s | ND z |
| | | N3 | 110 v | 8 xy | 450 s | 2.4 yz |
| B | 26 | None | ND z | 50 w | ND z | 60 w |
| | | N2 | 130 v | 4 y | 430 s | 0.7 z |
| | | N3 | 110 v | 2 z | 310 t | ND z |

[a] A-Nunn soil collected in early spring, B-Nunn soil collected in mid-summer.
[b] Small Colonies <30 mm diameter after 4 days of the Pythium selective medium - characteristic of the colony morphology of N2 and N3.
[c] Large colonies >50 mm diameter after 4 days on the Pythium selective medium - characteristic of *P. ultimum* (isolate N1).
[d] ND - not determined, numbers followed by the same letters are not significantly different (P = 0.05).

When Pythium isolates N2 or N3 were added to the soil (about 100 cfu/gm soil) increase in inoculum density of *P. ultimum* after one week was significantly lower than in soil which had not been infested with isolates N2 and N3 in both soils A and B and at both temperatures. A simultaneous increase (at least $2 \times 10^4$ cfu/gm) was observed in population densities of isolates N2 and N3. After two weeks of incubation a further decrease (in some cases to nondetectable levels), in the inoculate density of *P. ultimum* in those soils infested with isolates N2 and N3 was detected.

Influence of Pythium Isolates N2 and N3 on Damping-Off of Cucumber Induced By *P. ultimum*

Isolates N2 and N3 were added to soils A and B and leaf meal was added at two weekly intervals during the two weeks of incubation. In the control, isolates N2 and N3 were not added. In the controls, leaf meal additions resulted in an increase of inoculate density of *P. ultimum* within the two-week incubation period. The soils were added to raw soil A at concentrations of either 1 or 10% by weight. Emergence of cucumber seedlings was consistently and significantly improved at the 90% dilution over controls to which N2 and N3 were not added. Emergence, significantly better than the control, was not consistent at the 99% dilution. The results are shown below in TABLE 3.

TABLE 3

Preemergence damping-off of cucumbers induced by *Pythium ultimum* in soil to which isolates N2 or N3 or had not been added.

| Raw Soil in Mixture (%) | Temp. of Incubation (C.) | Control (%) | Healthy Plants N2 (%) | N3 (%) |
|---|---|---|---|---|
| 90 Batch A | 19 | 46.7 y | 86.7 v | 90.0 v |
| 99 Batch A | " | 70.0 wx | 83.3 v | 90.0 v |
| 90 Batch A | 26 | 60.0 x | 90.0 v | 86.7 v |
| 99 Batch A | " | 83.3 v | 83.3 v | 90.0 v |
| 90 Batch B | 19 | 30.0 z | 90.0 v | 70.0 wx |
| 99 Batch B | " | 66.7 x | 90.0 v | 63.3 x |
| 90 Batch B | 26 | 36.7 z | 76.7 v | 76.7 w |
| 99 Batch B | " | 63.3 x | 90.0 v | 83.3 v |
| A (nontreated) | | 90.0 v | | |

[a]A-Nunn soil collected early spring, B-Nunn soil collected in mid-summer.
[b]Isolates N2 and N3 were added to soils A and B and leaf meal was added at two weekly intervals during the two-weeks of incubation. In controls N2 and N3 were not added. These soils were added to raw soil (A) at concentrations of either 1 or 10% by weight.
[c]Numbers followed by the same letters are not significantly different (P = 0.05).

Having described the isolation and activity of the novel isolates according to the present invention, the following examples are presented and are not intended to limit the scope of the present invention.

EXAMPLE 1

Effect of Isolates N2 and N3 on Lysis and the Formation of New Sporangia by *P. ultimum* on Membranes Placed on Soil Soil from batch A was incubated at 26° (−0.3 bar moisture) with six weekly additions of ground dry bean leaves (0.3% w/w) and air-dried. Nonamended soil served as a control. Ten gram samples from each soil were mixed with 30 milligrams bean leaf meal and placed in 45 millimeter diameter plastic plates. The soil in each plate was mixed with 3.0 ml sterile deionized water and the soil surface was smoothed with a spatula. Sporangia of *P. ultimum* harvested from one-week old oatmeal and water cultures were washed three times in sterile deionized water and resuspended to give $3 \times 10^3$ sporangia ml. Aliquots of 0.3 ml. suspension were placed on each 26 mm diameter Nucleopore membranes, and placed on a millipore holder. The water was removed with suction and the membrane subsequently placed on the smooth soil surface. The plates were covered, placed in polyethylene bags and incubated at 26° C. for 2, 24, 48 and 72 hours. After incubation the membranes were removed from soil, placed on cotton blue for one minute, and prepared for microscopic observation by the methods of Sneh (*Soil Biol. and Biochem.* 9, 55–65 (1977) or Bristow, et al., *J. Gen. Microbiol.* 90 140–146 (1975)). All of the sporangia on each membrane were counted.

The sterile soil amended with 0.3% leaf meal was incubated with Pythium isolates N2 or N3. After two weeks of incubation, the soils were dried (population density $10^4$ cfu/gm soil) and tested for the effect of N2 and N3 on germination, lysis and formation of new sporangia. Two membranes for each treatment were used for each of three experiments. The results are shown below in TABLE 4.

TABLE 4

Effect of six weekly incorporations of bean leaves (0.3% w/w) into soil on germination, germtube lysis, and new sporangia formation by sporangia of *P. ultimum* placed on membranes on soil.

| Soil Treat.[a] | Germination (%) 24 h | Number Sporangia/Membrane Typical | | | Small | |
|---|---|---|---|---|---|---|
| | | Empty | New 20–24 μm | Ratio New:Empty[b] | New 10–15 μm | Ratio New:Empty |
| Nonamended | 98 | 675 z[d] | 1564 z | 2.30:1 z | 245 x | 0.36:1 x |
| Amended | 98 | 603 z | 230 y | 0.38:1 y | 842 y | 1.40:1 y |
| *P. ultimum*[c] | 98 | 775 z | 1742 z | 2.50:1 z | 302 x | 0.35:1 x |
| Pythium sp. N3 | 98 | 627 z | 132 x | 0.43:1 y | 1110 z | 1.8:1 z |
| Pythium sp. N2 | 98 | 639 z | 49 w | 0.08:1 x | 837 y | 1.3:1 y |

[a]Bean leaves (0.3%) were added to all treatments prior to placing the nuclepore membranes on soil (batch A).
[b]All sporangia were counted on each membrane after 48 h incubation. Empty sporangia were the germinated ones and the newly formed ones were full of protoplasm. Two membranes wre counted for each treatment. The experiment was repeated 3 times.
[c]Sporangia of *P. ultimum* added to raw soil ($10^4$ sporangia/g soil).
[d]Numbers in each column followed by the same letters are not significantly different (P = 0.05).

As seen above in TABLE 4, sporangia of *P. ultimum* placed on nuclepore membranes in soil germinated well (98%) in all treatments. However, hyphal lysis was much more advanced after 24 hours on the amended soil, while a considerable proportion of the hyphae in the nontreated soil remained intact. In this treatment, total lysis occurred at a later stage (48–72 hours). Germinated sporangia were empty while newly-formed sporangia were full of protoplasm. More new sporangia were formed from germinated sporangium on the control soil (2.3:1) than on the treated soil (0.38:1). However, more aborted small sporangia were formed in the amended soil (1.4:1) as compared to the control (0.36:1).

Pythium species isolates N2 and N3 grown in sterile soil induced germ tube lysis of *P. ultimum* on membranes in a similar manner to that of observed in the repeatedly amended soil described above. These isolates also reduced the number of typical new sporangia found on the membranes, and increased the number of small ones. The addition of *P. ultimum* to the soil ($10^4$ sporangia/grams per soil) did not induce any change in new sporangia formation.

EXAMPLE 2

Effect of Incubation Temperature, Soil pH and Trichoderma spp. on the Saprophytic Development of Pythium spp. in Soil Referring to FIG. 1, there is shown the effect of incubation temperature and soil (from batch A) pH on propagule density of *Pythium ultimum* during six weekly repeated incorporation of dried bean leaf meal (0.3% w/w). Bars indicate *P. ultimum* propagule density range (not significantly different), in a noninoculated control soil and in soils infested with $10^6$ conidia gm/soil of *Trichoderma harzianum* isolates T12, T95 and *T. koningii* T8 (T12 and T8 are available from N.Y. State Agricultural Experimental Station, Geneva, N.Y. 14456; T95 is available from Prof. Ralph Baker, Dept. of Botany, Colorado State Univ., Ft. Collins, CO 80523). When soil was repeatedly amended with bean leaf meal for 6 weeks, a sharp increase in population density of *P. ultimum* was observed after the first week from undetectable levels to $2.3 \times 10^2$ inoculum desnity in soil with pH 7.3 incubated in both temperatures (19° and 26° C.). However, a greater increase ($5 \times 10^3$ propagules/g) was recorded in the acidified soil (pH 5.0) at 26° C. In this treatment a further increase occurred up to the third week ($2 \times 10^4$ propagules/g) and then declined to $6 \times 10^3$ propagules/g after 6 weeks. In soil with pH 7.3, *P. ultimum* propagule density over time was significantly affected by incubation temperature. While at 19° C. population density increased gradually up to $4.5 \times 10^3$ propagules/g after 6 weeks, a gradual but steady decline occurred in soil incubated at 26° C.; after 6 weeks propagule density level was only 5 propagules/g.

Figure 2:
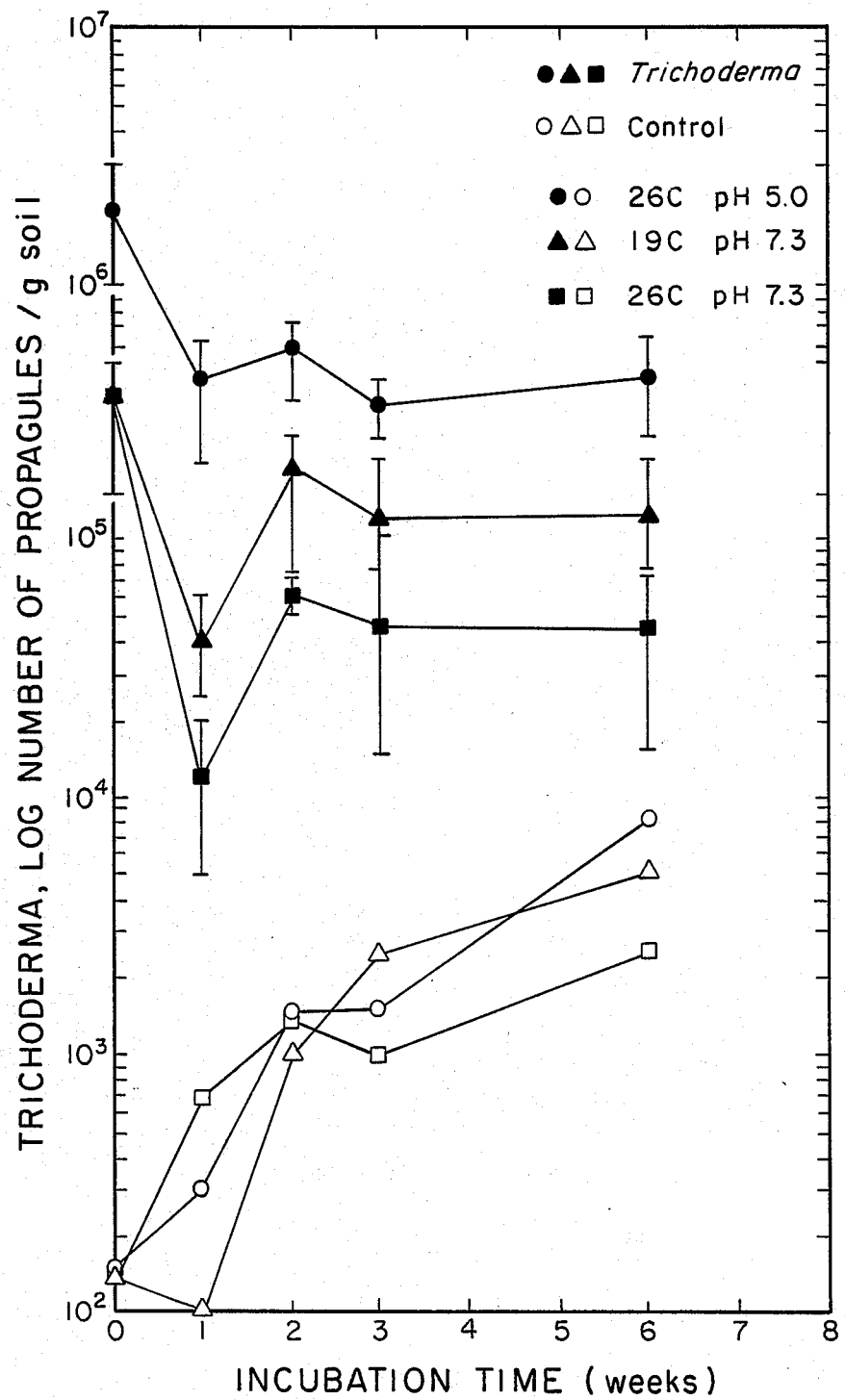
FIG. 2 is a plot of Trichoderma propagule density in soil at various pHs and temperatures to which Trichoderma species were and were not added.

Referring to FIG. 2, there is shown the effect of incubation temperature and soil (from batch A) pH on population density of *Trichoderma harzianum* isolates T12 and T95 and *T. koningii* T8, during six weekly repeated incorporations of dried bean leaf meal to soils infested with $10^6$ indigenous conidia Trichoderma soil at the beginning of the experiment. Bars indicate propagule densities range of the three isolates (not significantly different). In the soil to which Trichoderma spp. had not been added, population densities on the indigenous Trichoderma spp. gradually increased from $10^2$ to $2.8 \times 10^3$ cfu/g soil over the six week period. There was no effect of indigenous Trichoderma spp. on the inoculum density of *P. ultimum*.

Figure 3:
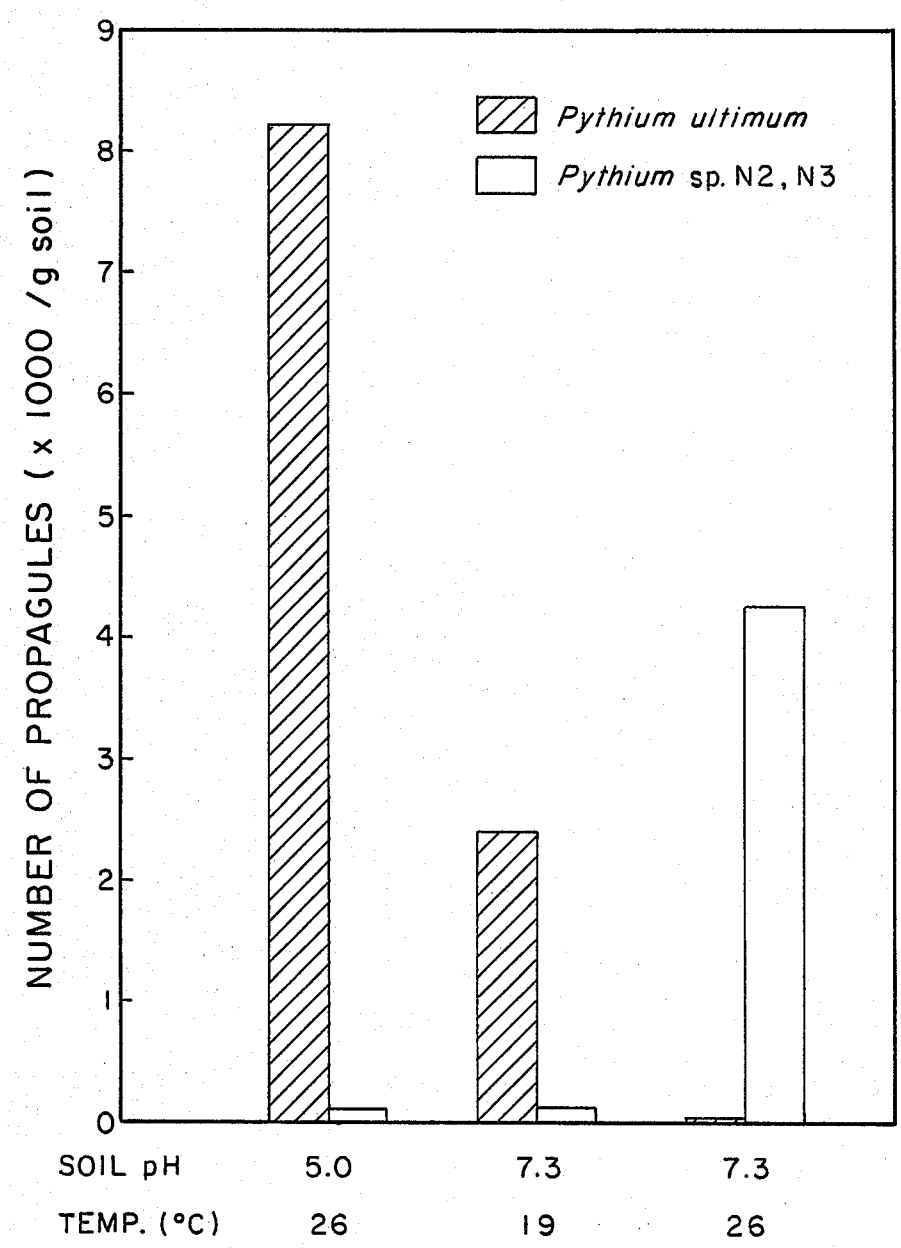
FIG. 3 is a plot of relative developed densities of *Pythium ultimum* versus Pythium sp. isolates N2 and N3 developed in soil at three temperatures and pHs.

Referring to FIG. 3, there is shown the effect of incubation temperature and soil (from batch A) pH on Pythium spp. propagule densities, as determined by soil dilutions on a selective medium after six weekly repeated incorporations of dried bean leaf meal. Colonies were counted on the plates after 4 days. *P. ultimum* formed colonies of >50 mm diam while Pythium sp. isolates N2 and N3 formed colonies of <30 mm diam.

At the end of the 6 week incubation, counts on a Pythium-selective medium were made separately for *P. ultimum* (large colonies) and for N2 and N3 type (small colonies) At 26° C. in soil of pH 5.0, there was a high inoculum density of *P. ultimum* ($8.2 \times 10^3$ cfu/g soil) while population densities of the N2 and N3 types were low (ca 100 cfu/g). However, a reverse situation occurred at the same temperature but in soil pH of 7.3. Population densities of Pythium types N2 and N3 increased to $4.25 \times 10^3$ cfu/g soil, while the inoculum densities of *P. ultimum* declined to less than 50 cfu/g soil. At the same soil pH (7.3), at lower temperature, population densities of N2 and N3 were low, while *P. ultimum* increased $2.4 \times 10^3$ cfu/g soil.

From the above tests it can be seen that while indigenous *Pythium ultimum* is pathogenic to many plants tested, the Pythium sp. isolates N2 and N3 were not. Thus, the isolates N2 and N3 are useful biocontrol agents against plant-pathogenic Pythium species. The N2 and N3 isolates are useful to induce suppressiveness in soil, particularly to seedling damping-off. As biocontrol agents, isolates N2 and N3 may have one or more of the following advantages: (1) as mycoparasites, they may reduce the density of an established inoculum of pathogenic Pythium species in soil; (2) these isolates may also increase their population density in raw soil, indicating a strong, competitive saprophytic ability in soil; (3) being taxonomically related to pathogenic Pythium species, these isolates may function as strong competitors and therefore suppress inoculum build-up of the pathogenic Pythium species. A further advantage is that suppressiveness of pathogenic Pythium species may be induced by an initial application of a relatively small amount of the biocontrol agent, followed by organic amendment, to provide a propagule build-up of the agent. Thus, the isolates according to the present invention are easily applied, efficient, and long-lasting biocontrol agents.

The biocontrol agents according to the present invention may be applied by methods known in the art, i.e., such as by mixing with conventional carriers for agricultural application to soil, vegetation, seeds, and the like. The rate of application of the microorganisms will depend upon the extent and locus of pathogenic Pythium infestation. Since the isolates according to the present invention will grow, the rate of application is not particularly critical. Typically, the isolates may be applied at the rate of about $10^5$ propagules/gm soil. It is preferred that the biocontrol agents according to the present invention be located in the subsurface of the soil where indigenous Pythium is known to proliferate, however, applications to the surface of the soil as well as to the surface of host plants or seeds may also be effective.

What is claimed is:

1. A biologically pure culture of Pythium isolate N2 having the identifying characteristics of ATCC 20692.

2. A biologically pure culture of Pythium isolate N3 having the identifying characteristics of ATCC 20693.

3. A method for suppressing in soil the growth of indigenous *Pythium ultimum* comprising the step of applying to said species of their growth environment a substantially biologically pure mycoparasitic fungal strain of Pythium isolate N2 having the identifying characteristics of ATCC 20692 or Pythium isolate N3 having the identifying characteristics of ATCC 20693.

4. A method for preventing damping-off disease in plant seedlings comprising the step of applying to the soil environment of said seedlings an amount of a fungal strain of Pythium isolate N2 having the identifying characteristics of ATCC 20692 or Pythium isolate N3 having the identifying characteristics of ATCC 20693 effective to prevent said disease.

5. A composition for suppressing growth of *Pythium ultimum* in soil comprising an amount of a fungal strain of Pythium isolate N2 having the identifying characteristics of ATCC 20692 or Pythium isolate N3 having the identifying characteristics of ATCC 20693 sufficient to suppress the growth of *Pythium ultimum* in soil and an agriculturally acceptable carrier.

* * * * *

UNITED STATES PATENT AND TRADEMARK OFFICE
CERTIFICATE OF CORRECTION

PATENT NO. : 4,574,083

DATED : March 4, 1986

INVENTOR(S) : Ralph Baker and Ran Lifshitz

It is certified that error appears in the above-identified patent and that said Letters Patent are hereby corrected as shown below:

Col. 3, line 12: Delete "mycleium" and insert --mycelium--.
Col. 5, line 10: After "N3" insert --had--.
Claim 3, line 45: Delete "of" and insert --or--.

Signed and Sealed this

First Day of July 1986

[SEAL]

Attest:

DONALD J. QUIGG

Attesting Officer

Commissioner of Patents and Trademarks